(12) United States Patent
Oved

(10) Patent No.: US 10,867,436 B2
(45) Date of Patent: Dec. 15, 2020

(54) SYSTEMS AND METHODS FOR RECONSTRUCTION OF 3D ANATOMICAL IMAGES FROM 2D ANATOMICAL IMAGES

(71) Applicant: Zebra Medical Vision Ltd., Shefayim (IL)

(72) Inventor: Amit Oved, Givatayim (IL)

(73) Assignee: Zebra Medical Vision Ltd., Shefayim (IL)

( * ) Notice: Subject to any disclaimer, the term of this patent is extended or adjusted under 35 U.S.C. 154(b) by 130 days.

(21) Appl. No.: 16/387,599

(22) Filed: Apr. 18, 2019

(65) Prior Publication Data
US 2020/0334897 A1    Oct. 22, 2020

(51) Int. Cl.
| | |
|---|---|
| G06K 9/00 | (2006.01) |
| G06T 17/00 | (2006.01) |
| A61B 6/03 | (2006.01) |
| G06T 11/00 | (2006.01) |
| G06T 7/00 | (2017.01) |
| A61B 6/00 | (2006.01) |
| G06N 3/02 | (2006.01) |
| G06T 7/33 | (2017.01) |

(52) U.S. Cl.
CPC ............ G06T 17/00 (2013.01); A61B 6/032 (2013.01); A61B 6/5211 (2013.01); G06K 9/00208 (2013.01); G06T 7/0012 (2013.01); G06T 11/008 (2013.01); G06N 3/02 (2013.01); G06T 7/33 (2017.01); G06T 2207/10072 (2013.01); G06T 2207/30004 (2013.01); G06T 2210/41 (2013.01)

(58) Field of Classification Search
None
See application file for complete search history.

(56) References Cited

U.S. PATENT DOCUMENTS

2002/0015934 A1 * 2/2002 Rubbert .................. A61C 7/00
433/29
2013/0144135 A1 * 6/2013 Mahfouz ................ A61B 34/10
600/309

(Continued)

OTHER PUBLICATIONS

European Search Report and the European Search Opinion dated Jul. 2, 2020 From the European Patent Office Re. Application No. 20163846.7. (10 Pages).

(Continued)

*Primary Examiner* — Shervin K Nakhjavan

(57) ABSTRACT

There is provided a method of training a neural network for reconstructing of a 3D point cloud from 2D image(s), comprising: extracting point clouds each represented by an ordered list of coordinates, from 3D anatomical images depicting a target anatomical structure, selecting one of the plurality of point clouds as a template, non-rigidly registering the template with each of the point clouds to compute a respective warped template having a shape of the respective point cloud and retaining the coordinate order of the template, wherein the warped templates are consistent in terms of coordinate order, receiving 2D anatomical images depicting the target anatomical structure depicted in corresponding 3D anatomical images, and training a neural network, according to a training dataset of the warped templates and corresponding 2D images, for mapping 2D anatomical image(s) into a 3D point cloud.

21 Claims, 7 Drawing Sheets

(56) References Cited

U.S. PATENT DOCUMENTS

| | | | |
|---|---|---|---|
| 2014/0163375 A1* | 6/2014 | Wasielewski | A61B 8/4427 |
| | | | 600/443 |
| 2014/0336461 A1* | 11/2014 | Reiter | A61B 1/06 |
| | | | 600/111 |
| 2014/0379356 A1* | 12/2014 | Sachdeva | A61C 7/002 |
| | | | 705/2 |
| 2015/0206003 A1* | 7/2015 | Haker | G06T 19/20 |
| | | | 345/420 |
| 2015/0328004 A1* | 11/2015 | Mafhouz | A61F 2/30942 |
| | | | 700/98 |
| 2016/0008083 A1* | 1/2016 | Kesten | A61B 34/20 |
| | | | 600/424 |
| 2016/0278678 A1* | 9/2016 | Valdes | A61B 1/00009 |
| 2018/0053347 A1* | 2/2018 | Fathi | G06T 17/05 |
| 2018/0168780 A1* | 6/2018 | Kopelman | A61B 34/10 |
| 2018/0189966 A1* | 7/2018 | Kamen | G06T 15/04 |
| 2018/0218507 A1* | 8/2018 | Hyllus | G06T 7/344 |
| 2018/0270474 A1* | 9/2018 | Liu | A61B 6/508 |
| 2018/0330496 A1* | 11/2018 | Ma | H04N 5/232 |
| 2018/0338742 A1* | 11/2018 | Singh | A61B 6/587 |
| 2018/0368917 A1* | 12/2018 | Dekel | A61B 34/20 |
| 2019/0200964 A1* | 7/2019 | Sudhakar | A61B 8/5223 |
| 2020/0121556 A1* | 4/2020 | Tian | A61H 39/04 |
| 2020/0194117 A1* | 6/2020 | Krieger | G16H 50/20 |
| 2020/0219272 A1* | 7/2020 | Pizer | G06T 7/507 |
| 2020/0226765 A1* | 7/2020 | Wood | G06K 9/6272 |
| 2020/0320775 A1* | 10/2020 | Holladay | G06T 7/11 |
| 2020/0320777 A1* | 10/2020 | Meshry | G06N 3/082 |

OTHER PUBLICATIONS

Achlioptas et al. "Representation Learning and Adversarial Generation of 3D Point Clouds", ArXiv Preprint ArXiv:1707.02392v1, XP080775240, Cornell University Library, p. 1-20, Jul. 8, 2017.

Henzler et al. "Single-Image Tomography: 3D Volumes From 2D Cranial X-Rays", ArXiv Preprint ArXiv: 1710.04867v3, XP081423943, Cornell University Library, p. 1-12, Nov. 28, 2018.

Mandikal et al. "3D-LMNet: Latent Embedding Matching for Accurate and Diverse 3D Point Cloud Reconstruction From a Single Image", ArXiv Preprint ArXiv:1807.07796v1, Cornell University Library, XP081250079, p. 1-19, Jul. 20, 2018.

Varol et al. "BodyNet: Volumetric Inference of 3D Human Body Shapes", ArXov Preprint ArXiv:1804.04875v3, XP081092112, Cornell University Library, p. 1-27, Aug. 18, 2018.

Wang et al. "MVPNet: Multi-View Point Regression Networks for 3D Object Reconstruction From a Single Image", ArXiv Preprint ArXiv:1811.09410v1, XP081053670, Cornell University Library, p. 1-8, Nov. 23, 2018.

* cited by examiner

SYSTEMS AND METHODS FOR RECONSTRUCTION OF 3D ANATOMICAL IMAGES FROM 2D ANATOMICAL IMAGES

FIELD AND BACKGROUND OF THE INVENTION

The present invention, in some embodiments thereof, relates to reconstruction of 3D images and, more specifically, but not exclusively, to reconstruction of a 3D anatomical image from a 2D anatomical image.

3D reconstruction is an important tool for diagnosis of pathologies and surgical planning, especially of skeletal related conditions. The most prominent and wide spread 3D imaging technology is the CT. CT is an accurate 3D imaging technology which produces high resolution information of the internal structure of the human body. This capability comes at a price—a CT scan induces high radiation dosage to the patient, it is relatively pricey, the CT scanner is immobile and it does not allow versatile patient positions during the scan—which might be important in some cases.

SUMMARY OF THE INVENTION

According to a first aspect, a method of training a neural network for reconstructing of a 3D point cloud from at least one 2D image, comprises: extracting a plurality of point clouds each represented by an ordered list of coordinates, from a plurality of 3D anatomical images depicting a target anatomical structure, selecting one of the plurality of point clouds as a template, non-rigidly registering the template with each of the plurality of point clouds to compute a respective warped template having a shape of the respective point cloud and retaining the coordinate order of the template, wherein the plurality of warped templates are consistent in terms of coordinate order, receiving a plurality of 2D anatomical images depicting the target anatomical structure depicted in corresponding 3D anatomical images, and training a neural network, according to a training dataset of the warped templates and corresponding 2D images, for mapping at least one 2D anatomical image into a 3D point cloud.

According to a second aspect, a method for surgical treatment of a target anatomical structure of a patient, comprises: obtaining a 2D anatomical image depicting a target anatomical structure of a target patient, inputting the 2D anatomical image into a trained neural network trained according to a training dataset of a plurality of warped templates and corresponding 2D images, wherein the plurality of warped templates are created from a plurality of point clouds extracted from a plurality of 3D anatomical images, each point cloud represented by an ordered list of coordinates, one of the plurality of point clouds is selected as a template, the template is non-rigidly registered with each of the plurality of point clouds to compute the plurality of warped template each having a shape of the respective point cloud and retaining the coordinate order of the template, wherein the plurality of warped templates are consistent in terms of coordinate order, and outputting a reconstructed 3D point cloud model of the target anatomical structure by the trained neural network, wherein surgical treatment of the target anatomical structure of the patient is planned according to the reconstructed 3D point cloud model of the target anatomical structure.

According to a third aspect, a system for training a neural network for reconstructing of a 3D point cloud from a 2D image, comprises: at least one hardware processor executing a code for: extracting a plurality of point clouds each represented by an ordered list of coordinates, from a plurality of 3D anatomical images depicting a target anatomical structure, selecting one of the plurality of point clouds as a template, non-rigidly registering the template with each of the plurality of point clouds to compute a respective warped template having a shape of the respective point cloud and retaining the coordinate order of the template, wherein the plurality of warped templates are consistent in terms of coordinate order, receiving a plurality of 2D anatomical images depicting the target anatomical structure depicted in corresponding 3D anatomical images, and training a neural network, according to a training dataset of the warped templates and corresponding 2D images, for mapping at least one 2D anatomical image into a 3D point cloud.

In a further implementation of the first, second, and third aspect, the plurality of 2D anatomical images comprise a plurality of emulated 2D anatomical images computed from each of the corresponding 3D anatomical images, by aggregating imaging values of the corresponding 3D anatomical image along a direction corresponding to an orientation of a virtual 2D sensor virtually capturing the emulated 2D anatomical image.

In a further implementation of the first, second, and third aspect, the plurality of emulated 2D anatomical images are computed to correspond to target 2D x-ray images captured by an x-ray source and x-ray sensor array at a predefined orientation relation to the patient.

In a further implementation of the first, second, and third aspect, each of the plurality of point clouds extracted from the plurality of 3D anatomical images denotes a 3D polygon mesh represented by coordinate order of the vertices and connections thereof.

In a further implementation of the first, second, and third aspect, each point cloud of the plurality of point clouds is extracted from a respective 3D anatomical image of the plurality of 3D anatomical images by: computing, for each 2D slice of a plurality of 2D slices of the respective 3D anatomical image, a 2D segmentation of the depicted target anatomical structure, stacking the plurality of 2D segmentations computed for the plurality of 2D slices, obtaining a 3D binary array of the target anatomical structure from the stacked plurality of 2D segmentations, and computing the point cloud from the 3D binary array.

In a further implementation of the first, second, and third aspect, the 2D segmentation of the depicted target anatomical structured is segmented from the respective 2D slice by a segmentation neural network that computes a pixel-wise probability of the respective pixel depicting the target anatomical structure, wherein the segmentation neural network is trained on a training dataset of a plurality of 2D slices of each a plurality of 3D anatomical images of a plurality of sample patients, wherein each 2D slice is annotated with an indication of a segmentation of the target anatomical structure.

In a further implementation of the first, second, and third aspect, the non-rigidly registering is performed according to a non-rigid registration process selected from coherent point drift and non-rigid iterative closest points.

In a further implementation of the first, second, and third aspect, the target anatomical structure includes a joint and associated bones, selected from the group consisting of: a hip joint, a knee joint, and a shoulder joint.

In a further implementation of the first, second, and third aspect, the target anatomical structure comprises a bone.

In a further implementation of the first, second, and third aspect, the target anatomical structure comprises a femur.

In a further implementation of the first, second, and third aspect, the target anatomical structure includes an inner surface of a bone.

In a further implementation of the first, second, and third aspect, the inner surface comprises an inner surface of a cortical bone.

In a further implementation of the first, second, and third aspect, the inner surface is of a medullary cavity of a long bone.

In a further implementation of the first, second, and third aspect, the reconstructed 3D point cloud model of the target anatomical structure includes an internal surface thereof.

In a further implementation of the first, second, and third aspect, the target anatomical structure comprises a long bone and the internal surface depicted in the reconstructed 3D point cloud comprises an inner surface of a medullary cavity of the long bone.

In a further implementation of the first, second, and third aspect, the 2D anatomical images comprises an x-ray image.

In a further implementation of the first, second, and third aspect, further comprising: computing a projection for projecting the reconstructed 3D model on the plane of the 2D image, wherein the 2D anatomical image includes a depiction of a calibration object having known dimensions, computing a scale parameter of the projection, scaling the reconstructed 3D model from original arbitrary units to pixel units according to the scale parameter, computing a conversion parameter for converting from pixel units to millimeters according to the calibration object depicted in the 2D anatomical image, and converting the pixel units of the reconstructed 3D image to millimeters according to the computed conversion parameter.

In a further implementation of the first, second, and third aspect, the target anatomical region comprises at least one bone, and surgical treatment of the patient planned according to the reconstructed 3D point cloud model of the target anatomical structure comprises selecting at least one of a joint replacement prosthetic and a fracture repair implantable device according to at least one dimension of the at least one bone depicted by the 3D point cloud model.

In a further implementation of the first, second, and third aspect, surgical treatment of the patient planned according to the reconstructed 3D point cloud model of the target anatomical structure comprises simulating a surgical procedure using the 3D point cloud model.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a flowchart of a method of training a neural network for reconstruction of a 3D point cloud depicting a target anatomical structure from one or more 2D images depicting the target anatomical structure, in accordance with some embodiments of the present invention;

FIG. 2 is a block diagram of components of a system for training a neural network for reconstruction of a 3D point cloud depicting a target anatomical structure from one or more 2D images depicting the target anatomical structure and/or for surgical treatment of a target anatomical structure of a patient according to a 3D point cloud reconstruction of the target anatomical structure outputted by the neural network, in accordance with some embodiments of the present invention;

Figure 6:
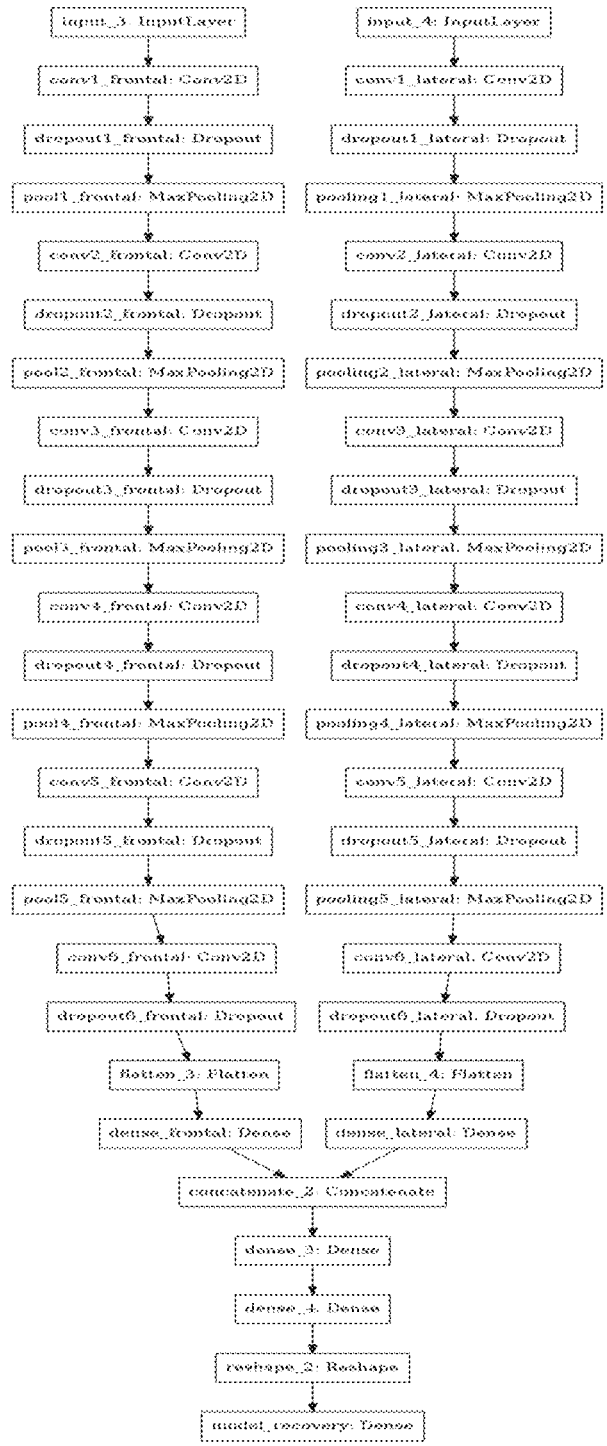
Figure 7:
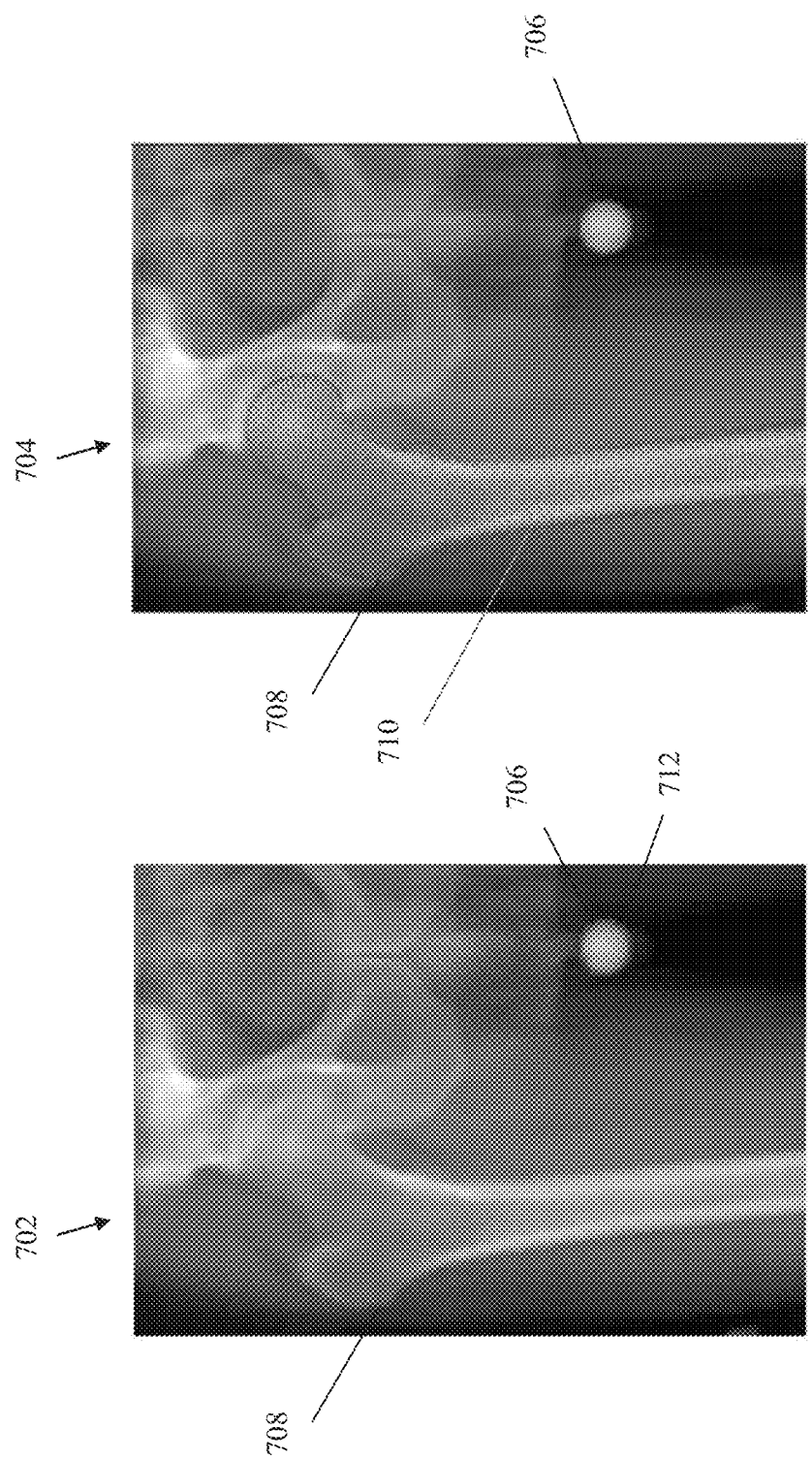

FIG. 6 is a diagram depicting an exemplary architecture of the neural network for mapping two 2D anatomical images into a 3D point cloud, in accordance with some embodiments of the present invention; and FIG. 7 is 2D x-ray images depicting use of a calibration object placed to a femur, where the calibration object is automatically detected and measured for converting the size of a reconstructed 3D point cloud of the femur from arbitrary units to real world size, in accordance with some embodiments of the present invention.

DESCRIPTION OF SPECIFIC EMBODIMENTS OF THE INVENTION

An aspect of some embodiments of the present invention relates to systems, methods, an apparatus, and/or code instructions (i.e., stored in a memory and executable by hardware processor(s)) for training a neural network for reconstruction of a 3D point cloud depicting a target anatomical structure from one or more 2D images depicting the target anatomical structures, optionally 2D images at different orientations, for example, an x-ray image, and/or an ultrasound image, for example, anterior-posterior (AP) and lateral x-rays. Effectively, the neural network enables using 2D images acquired from a 2D imaging machine to generate 3D reconstructions of target anatomical structures, for example, in place of using a 3D imaging machine such as CT. Point clouds are extracted from 3D anatomical images depicting a target anatomical structure, optionally a bone, optionally a long bone, for example, a femur. A single point cloud may be extracted from each image. Each point cloud is represented by an ordered list of coordinates. One of the point clouds is selected as a template. The template is non-rigidly registered with each of the other point clouds to compute a respective warped template. The warped template has a shape of the respective point cloud and retains the coordinate order of the template. The warped templates are consistent in terms of coordinate order. Multiple 2D anatomical images depicting the target anatomical structure are received. Optionally, the 2D images depict the same target anatomical structure that is depicted in the corresponding 3D anatomical images, for example, 2D images may be created from the corresponding 3D anatomical images. A neural network is trained according to a training dataset of the warped templates and corresponding 2D images. The neural network is trained to receive one or more 2D anatomical images depicting the target anatomical structure, and output a 3D point cloud reconstruction of the target anatomical structure.

An aspect of some embodiments of the present invention relates to systems, methods, an apparatus, and/or code instructions (i.e., stored in a memory and executable by hardware processor(s)) for surgical treatment of a target anatomical structure of a patient based on a 3D reconstruction of a target anatomical structure depicted in a 2D anatomical image(s), for example, an x-ray. The 2D anatomical image(s) depicting the target anatomical structure of a target patient is received. The 2D anatomical image(s) is fed into a neural network trained according to a training dataset of warped templates and corresponding 2D images, as described herein. A reconstructed 3D point cloud model of the target anatomical structure is outputted by the trained neural network. Surgical treatment of the target anatomical structure of the patient is planned according to the reconstructed 3D point cloud model of the target anatomical structure. For example, a surgeon may view the 3D point cloud in order to plan the surgery. In another example, the 3D point cloud is fed into an application (and/or other code process) which aids in planning the surgery, for example, an application designed to measure medullar cavities of long bones for selection of prosthetic devices and/or nails for joint replacement and/or fracture repair and/or surgical simulation.

At least some implementations of the systems, methods, apparatus, and/or code instructions described herein address improve the technical field of neural networks, by enabling neural networks to map 2D images to 3D point clouds. At least some implementations of the systems, methods, apparatus, and/or code instructions described herein address the technical problem of training a neural network using a dataset of 3D point clouds, for example, 3D polygon meshes. Standard approaches cannot be used to train a neural network to map 2D image to 3D point clouds, since the neural network cannot be trained on a training dataset of 3D point clouds, for example, represented as 3D polygon meshes using standard approaches. While polygon meshing is an efficient way to describe surfaces, it lacks the property of a consistent representation which is required for training neural networks. Consistency in this context means that when a 3D structure is defined as a list of numbers, the order of the elements in that list cannot be shuffled without affecting the object it describes. For instance—a pixelated digital anatomical image (e.g., x-ray) is an ordered list of numbers. When that list is shuffled, the image described by the shuffled list is different than the original. The technical solution to the problem of polygon meshes do not possess this quality. They are described by a list of the vertex coordinates and their connectivity. If that list is shuffled and the connectivity is changed accordingly, the mesh this shuffled list described will be exactly the same as the original. Since polygon meshes representation lack consistency, the spatial relations between elements in one list are not conserved in another list describing similar object. Therefore, a neural network trained on polygon meshes, which lack consistency and do not conserve spatial relations between elements, will yield incorrect and/or irrelevant results. At least some implementations of the systems, methods, apparatus, and/or code instructions described herein provide a technical solution to the technical problem by selecting a single 3D point cloud from the training dataset, and using the selected 3D point cloud as a template. The template model (e.g., denoted T) is registered (optionally in a non-rigid fashion) until alignment with a different 3D point cloud model (e.g., denoted M) to compute a respective warped template. The warped template (e.g., denoted W) has the shape of M and yet retains the same vertex order of T. Repeating this process over the remaining point clouds in the training dataset creates a new dataset of 3D models which capture the shapes of the models in the original dataset and are consistent in terms of their vertex list ordering. The new dataset of warped templates, which are consistent in terms of their vertex list ordering, are used to train the neural network.

At least some implementations of the systems, methods, apparatus, and/or code instructions described herein address the technical problem of reconstruction of 3D images depicting a target anatomical structure of a patient from 2D images depicting the target anatomical structure of the patient. A 2D anatomical image such as an x-ray (also referred to herein as a radiograph) is a safe, reliable, cheap, widespread, and more flexible alternative in comparison to 3D CT images. Since x-rays are 2D projections of the body of the patient, they convey much less information than a 3D volume produced by a CT scanner. Reconstruction of the 3D anatomical structure from one or more 2D x-ray images is a challenging technical problem.

At least some implementations of the systems, methods, apparatus, and/or code instructions described herein improve the technological field of image processing, by enabling the use of 2D anatomical images to reconstruct 3D anatomical images.

At least some implementations of the systems, methods, apparatus, and/or code instructions described herein improve the field of medicine and/or medical treatment of a patient, by enabling the use of 2D anatomical images such as x-rays to view reconstructed 3D images of target anatomical structures of the patient. Treatment of the patient, such as surgical treatment, may be planned and/or simulated based on the reconstructed 3D images. Using 2D images instead of 3D images has several important advantages for treatment of patients, for example, relatively lower radiation, lower cost, faster acquisition time, and provides high quality treatment planning for patients where 3D imaging devices are unavailable.

At least some implementations of the systems, methods, apparatus, and/or code instructions described herein are different than other processes for reconstructing 3D anatomical images from 2D anatomical images, and/or provide advantages over such known processes. For example:

Point-based processes. In their simplest form—a skilled person manually annotates pairs of predefined key-points from a pair of radiographs with known orientation. Based on the key-point pairs' position on the images, and the orientation of the source and the film (or sensor), the 3D coordinates are estimated. Given a set of predefined key-points 3D coordinates, a generic 3D model is distorted such that it best explains the estimated key-points positions. However, the point-based models produce poor results and take a long time to for a skilled annotator to annotate.

An improvement to the point-based methods enabled single key-points to be used as well (not only stereo pairs). While stereo-pair's 3D position may be easily estimated, a single key-point's position in 3D cannot be estimated directly but is constrained to lie on the line connecting the X-ray source and the key-point's position on the image plane. Several such constraints lead to optimal distortion of a generic 3D model which best explains the input constraints. Such methods usually allow the annotator to annotate more key-points because pairing is not mandatory. As a result, the output models of such point-based methods are relatively more accurate and take less time to annotate. However, even such-point based methods are quite limited in the output accuracy (due to the small number of distinct key points), do not work well on continuous, featureless structures and/or regions (e.g., kneed joint), are heavily dependent on the operator skills and require long manual process of keypoint detection and pairing.

In contrast, at least some implementations of the systems, apparatus, methods, and/or code instructions described herein are highly accurate due to the large number of points in the reconstructed 3D point cloud, work well on featureless regions, and are relatively fast Some examples of other approaches for computing 3D models from 2D input images are now discussed, along with the improvement of at least some implementations of the systems, apparatus, methods, and/or code instructions described herein over the cited approaches. The following standard processes all rely on manual/semi-automated identification of a set of key points or curves on the X-ray image(s) followed by a reconstruction of the 3D object which best explains the location and shape of the identified key points and curves. The features are chosen by the researcher (or other trained user) and are identified either by visual inspection or by classical computer vision techniques. Most of the features in the described approaches are based on hand crafted processes, for example, Hough transform, active contours, watershed, and the like Like all hand crafted features, the features used in other processes are not chosen or parameterized by some optimization process (as done by at least some implementations of the systems, apparatus, methods, and/or code instructions described herein) and as a result—the features of standard approaches lead to sub-optimal results. In contrast, at least some implementations of the systems, apparatus, methods, and/or code instructions described herein are based on a trained neural network that extracts a set of features from an input 2D images, where the features are optimal for the task of outputting a 3D point cloud. The neural network is different than standard approaches such as a keypoints detection scheme, a standard segmentation scheme, and/or standard 2D to 3D conversion schemes. At least some implementations of the neural network described herein solve the problem of 2D image to 3D point cloud model in a single stage, which is robust to noise and/or poor image quality, is fully automatic, accurate, is computationally efficient, and/or is performed with relatively short processing time.

Contour-based processes. The principle of Contour-based processes is to associate identifiable 2D-contours from radiographs to 3D curves defined on the surface of a reference object. The process starts with an initial guess of the 3D structure and orientation of the object based on existing processes. Once the initial model is calculated, a 3D curve is chosen on the objects' surface such that its projection aligns with the model's projected silhouette (e.g., where the simulated X-rays are tangent to the 3D model's surface). The 3D curves are then projected on the image plane. From each pair of 2D curves (e.g., the radiograph bone contour and the 3D curve projection) a difference term is calculated which is then used to update the 3D model's shape. This process is repeated until convergence is reached. This process is also referred to as "non stereo corresponding contour" (NSCC) in contrast to the previously described "non stereo corresponding points" (NSCP) process. Contour-based processes allow 3D modeling of smoother surfaces (without distinct key points), produce more accurate models and significantly reduce the manual annotation time.

Statistical shape model (SSM) based processes. SSM processes pose powerful constraint on the output model by forcing it to be "naturally looking". This constraint allows higher levels of automation by replacing the human annotator's previous knowledge of the typical shape and possible variations of a natural reference object. Those processes require a large dataset of reference object models in order to compute the mean and variation of the entire collection of reference objects. Since all natural reference objects have similar structure and are highly correlated, dimensionality reduction may be used to simplify the final model estimation process and to enforce "naturalness". Usually, dimensionality reduction is achieved by calculation of the first few principal components of the statistical model using principal component analysis (PCA). Linear combinations of those vectors describe "naturally looking" reference objects. For example, once a set of radiographs is provided, an initial 3D model is projected on the image planes (similarly to the contour based methods) and the projected model's outline is compared to the estimated reference object's outline on the radiograph. The next step is an iterative process which is used to minimize the difference between the two curves (projected model's outline and the reference object outline) by varying the principal vectors' coefficients until a convergence is reached. SSM are computationally intense and therefore—take up to several minutes for a single object reconstruction.

Parametric process. Parameter processes present high levels of automation and accuracy as SSM but do so in a different fashion. A simplified parametric model is defined which is used to represent the object's shape. The parametric model is made of points, lines, cones, spheres, cylinders etc. termed descriptors. By applying the simplified parametric model on a large collection of object models, a statistical model is calculated and is used for inference. When a set of radiographs is provided, the main descriptors are calculated according to the identified anatomical landmarks and the full set of descriptors is estimated according to the statistical model. From the full set of descriptors, a personalized parametric model is obtained. In order to render the parametric model to a more natural looking model, a 3D generic mesh is morphed to fit the personalized parametric model.

At least some implementations of the systems, methods, apparatus, and/or code instructions described herein address the technical problem of converting a 3D point cloud by a neural network that is fed a 2D image, where the 3D point cloud is represented by an arbitrary coordinate system that is different than the coordinate system of the 2D image. Due to the nature of radiographic imaging, a position dependent magnification occurs where objects laying on a sphere centered around the x-ray source with small radius seem larger that objects laying on larger spheres. Since a radiograph is a projection of an entire volume of objects in different positions on a 2D plane, there is not a single scale parameter which can be used to convert object size in pixels to real world size (for instance—in millimeters). This is true even if the x-ray source, the patient and the detector positions and orientations are known. For some clinical applications, not only the shape but also the actual size of the object of interest are important. Using standard approaches, an object with known dimensions (i.e., a calibration object), is placed at the same distance from the x-ray source as the object of interest. Since the dimensions of the object are known, pixels to millimeters conversion parameter may be estimated. This parameter is relevant to objects located at the same distance to the x-ray source as the calibration object. Using it to measure different object appearing in the image is straightforward. However, at least some implementations of the neural network described herein do not directly map pixels to millimeters as is come in standard approaches. The problem of finding the right scaling parameter has another level of complexity and that is that the 3D point cloud model outputted by the neural network has some arbitrary coordinate system which is different than that of the input 2D image (e.g., radiograph). Therefore—pixels to millimeters conversion, which is used in standard approaches, can't be used to convert the 3D object from some arbitrary units to millimeters. At least some implementations of the systems, methods, apparatus, and/or code instructions described herein provide a technical solution to the described problem, by projecting the 3D model on the 2D image (e.g., radiograph) plane. Once the projection is found, the scaling parameter that was used for the projection is used to scale the estimated (not the projected) 3D model from its original arbitrary units to pixel units. Once the 3D model is scaled to pixel units, the calibration object in the image may be used to compute a pixels to millimeters conversion parameter which is then used to convert the 3D model to real world size.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1:
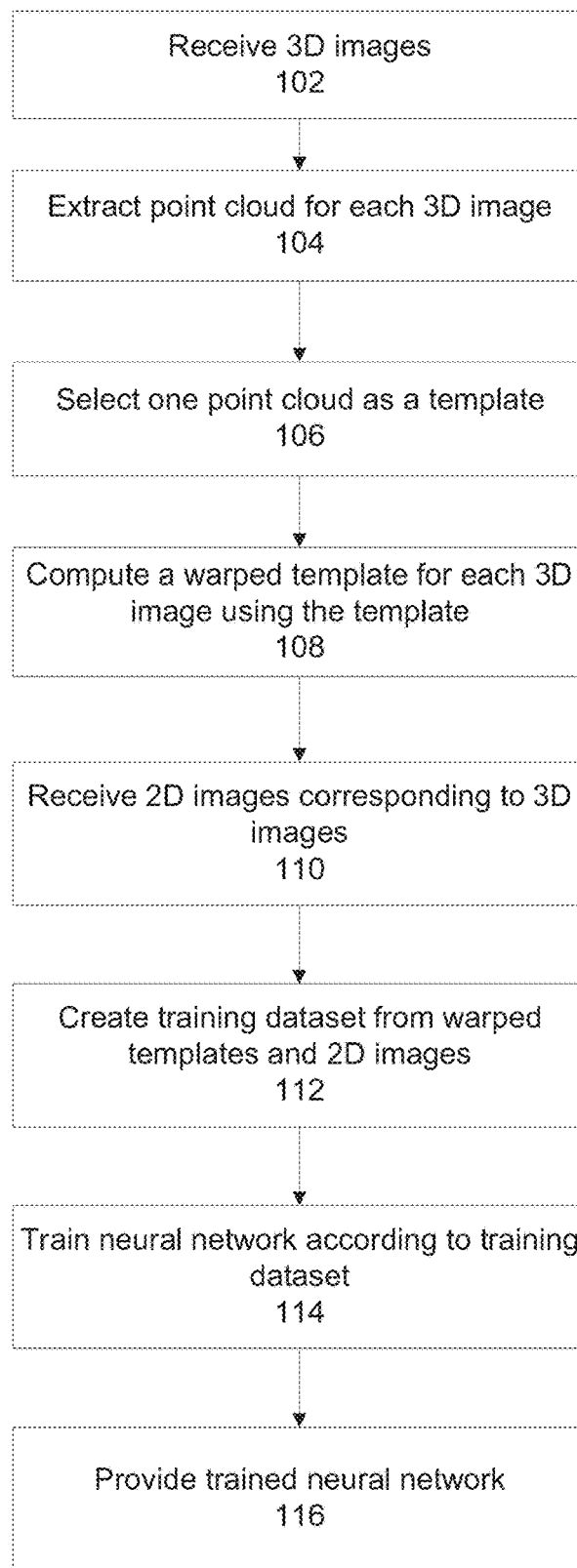
Figure 2:
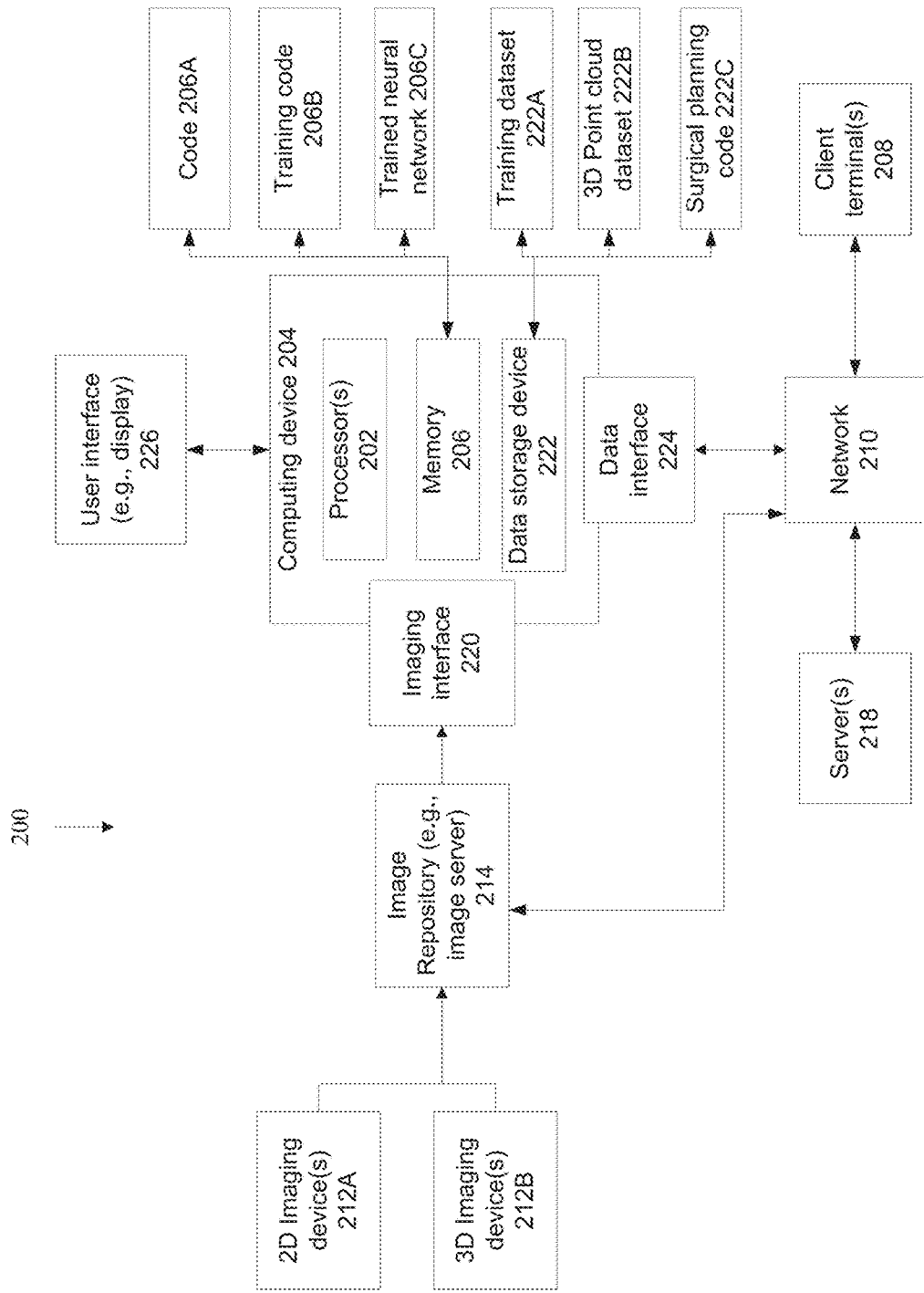
Figure 3:
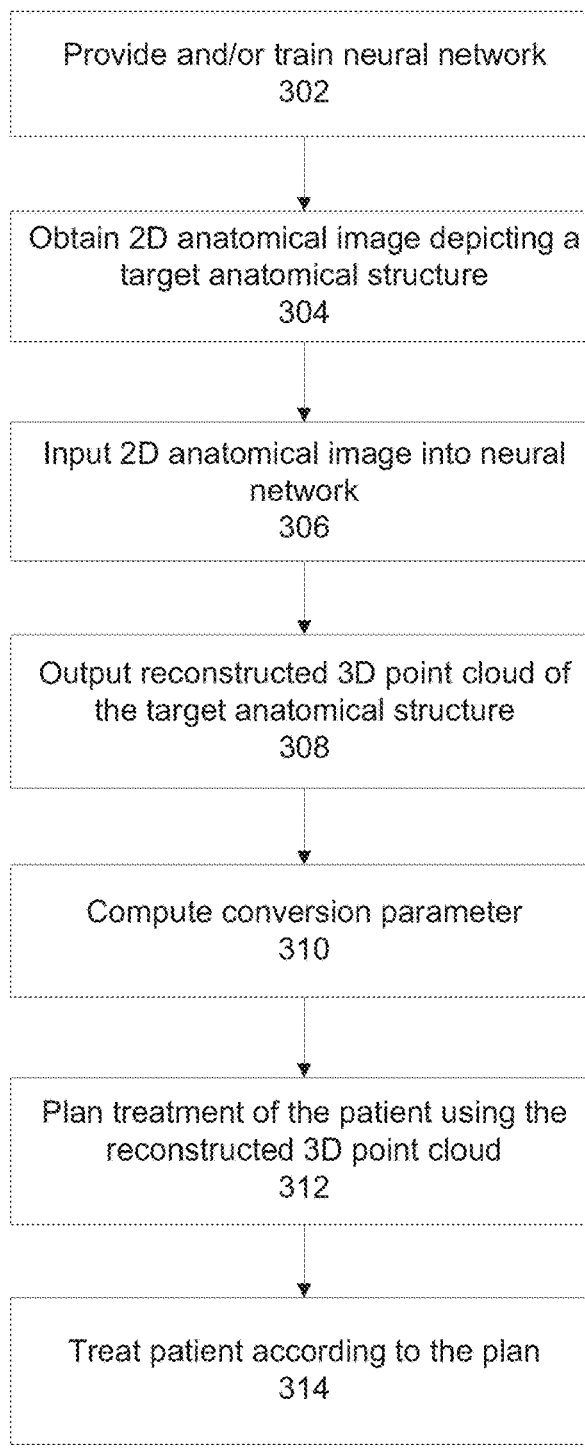
FIG. 3 is a flowchart of a method of surgical treatment of a target anatomical structure of a patient according to a 3D point cloud reconstruction of the target anatomical structure outputted by a neural network, in accordance with some embodiments of the present invention.

Reference is now made to FIG. 1, which is a flowchart of a method of training a neural network for reconstruction of a 3D point cloud depicting a target anatomical structure from one or more 2D images depicting the target anatomical structure, in accordance with some embodiments of the present invention. Reference is also made to FIG. 2, which is a block diagram of components of a system 200 for training a neural network for reconstruction of a 3D point cloud depicting a target anatomical structure from one or more 2D images depicting the target anatomical structure and/or for surgical treatment of a target anatomical structure of a patient according to a 3D point cloud reconstruction of the target anatomical structure outputted by the neural network, in accordance with some embodiments of the present invention. Reference is also made to FIG. 3, which is a flowchart of a method of surgical treatment of a target anatomical structure of a patient according to a 3D point cloud reconstruction of the target anatomical structure outputted by a neural network, in accordance with some embodiments of the present invention. System 200 may implement the acts of the method described with reference to FIG. 1 and/or FIG. 3, optionally by a hardware processor(s) 202 of a computing device 204 executing code instructions stored in a memory 206.

An exemplary implementation of reconstructing a 3D point cloud of a target anatomical structure of a patient according to a 2D anatomical image (e.g., x-ray) is now described to help understand system 200. A 2D imaging device 212A (e.g., x-ray machine) acquires a 2D anatomical image(s) of a target individual depicting a target anatomical structure. The 2D image(s) may be stored in an image repository 214, for example, a PACS server, a cloud storage, a storage server, CD-ROMs, and in an electronic health record. Computing device 204 computes the reconstructed 3D point cloud from the 2D anatomical image by executing code 206A which utilizes trained neural network code 206C, as described herein. Trained neural network 206C is generated by training code 206B from a training dataset 222A of warped templates created from 3D anatomical images outputted by 3D imaging device(s) 212B (e.g., CT scan) and corresponding 2D images optionally created from the 3D images. The reconstructed 3D point cloud may be stored in a 3D point cloud dataset 222B. Surgical treatment of the target anatomical structure of the patient may be planned using surgical treatment code 222C and using the reconstructed 3D point cloud model of the target anatomical structure.

Computing device 204 may be implemented as, for example, a client terminal, a server, a virtual server, a radiology workstation, a surgical planning workstation, a virtual machine, a computing cloud, a mobile device, a desktop computer, a thin client, a Smartphone, a Tablet computer, a laptop computer, a wearable computer, glasses computer, and a watch computer. Computing 204 may include an advanced visualization workstation that sometimes is add-on to a radiology workstation and/or surgical workstation and/or other devices for enabling the user to view the reconstructed 3D point cloud and/or plan surgery (and/or other treatments) using the reconstructed 3D point cloud.

Computing device 204 may include locally stored software that performs one or more of the acts described with reference to FIG. 1 and/or FIG. 3, and/or may act as one or more servers (e.g., network server, web server, a computing cloud, virtual server) that provides services (e.g., one or more of the acts described with reference to FIG. 1 and/or FIG. 3) to one or more client terminals 208 (e.g., client terminal used by a user for viewing anatomical images, client terminal running surgical planning application(s) for planning surgery using the reconstructed 3D point cloud, client terminal running computer aided diagnosis (CAD) application(s) for automated analysis of the reconstructed 3D point cloud, remotely located radiology workstations, remote picture archiving and communication system (PACS) server, remote electronic medical record (EMR) server) over a network 210, for example, providing software as a service (SaaS) to the client terminal(s) 208, providing an application for local download to the client terminal(s) 208, as an add-on to a web browser and/or a medical imaging viewer application and/or surgical planning application, and/or providing functions using a remote access session to the client terminals 208, such as through a web browser, application programming interface (API), and/or software development kit (SDK), for example, for integrating surgical planning applications with the computing device 204 to enable the surgical planning application to obtain the reconstructed 3D point cloud of the target anatomical structure(s) that the surgical application is designed for.

Client terminal(s) 208 may be implemented as, for example, a surgical planning workstation, a radiology workstation, a desktop computer (e.g., running a PACS viewer application and/or CAD application and/or surgical planning application), a mobile device (e.g., laptop, smartphone, glasses, wearable device), and nurse station server.

Is it noted that the training of the neural network, and the application of the trained neural network to 2D anatomical images to compute the reconstructed 3D point cloud, may be implemented by the same computing device 204, and/or by different computing devices 204, for example, one computing device 204 trains the neural network, and transmits the trained neural network to another server device 204 which uses the trained neural network to compute reconstructed 3D point clouds for 2D anatomical images.

Computing device 204 receives 2D anatomical images captured by 2D imaging device(s) 212A (e.g., x-ray, ultrasound) for computation of the reconstructed 3D point cloud. Alternatively or additionally, computing device 204 receives 3D anatomical images captured by 3D imaging device(s) 212B (e.g., CT, MRI, 3D ultrasound, nuclear scan) for creation of the training dataset 222A for training the neural network to create trained neural network 206C. 2D and/or 3D images may be stored in an image repository 214, for example, a storage server (e.g., PACS server), a computing cloud, virtual memory, and a hard disk.

Training dataset 222A is created from the captured 3D anatomical images as described herein.

2D anatomical images captured by 2D imaging device(s) 212A depict anatomical features and/or anatomical structures within the body of the target patient. 3D anatomical images captured by 3D imaging device(s) 212B are used to train the neural network for reconstructing 3D point clouds from 2D anatomical images captured by 2D imaging device(s) 212A, as described herein. Exemplary target anatomical structures depicted by 3D anatomical images, which are also depicted by the 3D point cloud reconstructed from the 2D anatomical image includes: joint and associated bones, for example, a hip joint, a knee joint, and a shoulder joint, a bone (e.g., femur), an inner surface of a bone optionally a cortical bone, and/or a medullary cavity of a long bone.

Computing device 204 may receive the 2D anatomical images and/or 3D anatomical images from imaging device(s) 212A and/or 212B and/or image repository 214 using one or more imaging interfaces 220, for example, a wire connection (e.g., physical port), a wireless connection (e.g., antenna), a local bus, a port for connection of a data storage device, a network interface card, other physical interface implementations, and/or virtual interfaces (e.g., software interface, virtual private network (VPN) connection, application programming interface (API), software development kit (SDK)).

Hardware processor(s) 202 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 202 may include one or more processors (homogenous or heterogeneous), which may be arranged for parallel processing, as clusters and/or as one or more multi core processing units.

Memory 206 (also referred to herein as a program store, and/or data storage device) stores code instruction for execution by hardware processor(s) 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). For example, memory 206 may store code 206A that implement one or more acts and/or features of the method described with reference to FIG. 1, and/or training code 206B that execute one or more acts of the method described with reference to FIG. 3, and/or code instructions of trained neural network 206C and/or surgical planning code 222C.

It is noted that surgical planning code 222C may include and/or be substituted for CAN applications and/or other applications that perform simulations and/or other computations using the reconstructed 3D point cloud model computed from 2D anatomical image(s).

Alternatively or additionally, client terminal(s) 208 and/or server 218 may locally store and/or execute surgical planning code 222C and/or training code 206B.

Computing device 204 may include a data storage device 222 for storing data, for example, trained dataset 222A (created as described herein), 3D point cloud dataset 222B (e.g., that stores the reconstructed 3D point clouds and/or computed 3D point clouds for inclusion in the training dataset), and/or surgical planning application(s) 222C. Data storage device 222 may be implemented as, for example, a memory, a local hard-drive, a removable storage device, an optical disk, a storage device, and/or as a remote server and/or computing cloud (e.g., accessed over network 210). It is noted that code 222A-C may be stored in data storage device 222, with executing portions loaded into memory 206 for execution by processor(s) 202.

Computing device 204 may include data interface 224, optionally a network interface, for connecting to network 210, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing device 204 may access one or more remote servers 218 using network 210, for example, to download updated training datasets, to download components for inclusion in the training datasets (e.g., 3D anatomical images) and/or to download an updated version of code 206A, training code 206B, trained neural network 206C, and/or surgical planning code 222C.

It is noted that imaging interface 220 and data interface 224 may be implemented as a single interface (e.g., network interface, single software interface), and/or as two independent interfaces such as software interfaces (e.g., as APIs, network ports) and/or hardware interfaces (e.g., two network interfaces), and/or combination (e.g., single network interface, and two software interfaces, two virtual interfaces on a common physical interface, virtual networks on a common network port). The term/component imaging interface 220 may sometimes be interchanged with the term data interface 224.

Computing device 204 may communicate using network 210 (or another communication channel, such as through a direct link (e.g., cable, wireless) and/or indirect link (e.g., via an intermediary computing device such as a server, and/or via a storage device) with one or more of:

Client terminal(s) 208, for example, when computing device 204 acts as a server that computes the reconstructed 3D point cloud from a provided 2D anatomical image. Client terminal 208 may provide the 2D anatomical image and receive the reconstructed 3D point cloud computed by computing device 204. The obtained reconstructed 3D point cloud may be, for example, presented within a viewing application for viewing (e.g., by a radiologist) on a display of the client terminal, and/or fed into surgical planning code 222C (and/or other application such as CAD) installed on client terminal 208).

Server 218. In one implementation, server 218 is implemented as image server 214, for example, a PACS server. Server 218 may store new 2D anatomical images as they are captured, and/or may store 3D anatomical images used for creating training dataset 222A. In another implementation, server 218 is in communication with image server 214 and computing device 204. Server 218 may coordinate between image server 214 and computing device 204, for example, transmitting newly received 2D anatomical images from server 218 to computing device 204 for computation of the reconstructed 3D point cloud. In yet another implementation, server 218 may perform one or more features described with reference to client terminal(s) 208, for example, feeding the reconstructed 3D point cloud into surgical planning application(s) 222C (which may be locally installed on server) 218.

Anatomical image repository 214 that stores 2D anatomical images (and/or 3D anatomical images for inclusion in the training dataset) and/or imaging device 212 that outputs the 2D anatomical images and/or 3D anatomical images.

Computing device 204 and/or client terminal(s) 208 and/or server(s) 218 include or are in communication with a user interface 226 that includes a mechanism designed for a user to enter data (e.g., select target anatomical structure(s) for computation of the reconstructed 3D point cloud, select surgical planning applications for execution) and/or view the obtained 2D images and/or view the reconstructed 3D point cloud. Exemplary user interfaces 226 include, for example, one or more of, a touchscreen, a display, a keyboard, a mouse, and voice activated software using speakers and microphone.

Referring now back to FIG. 1, at 102, multiple 3D images of sample patients are received. The 3D images depict the target anatomical structure, for example, joint and associated bones, for example, a hip joint, a knee joint, and a shoulder joint, a bone (e.g., femur), an inner surface of a bone optionally a cortical bone, and/or a medullary cavity of a long bone.

The 3D images may be outputted, for example, by a CT machine, an MRI machine, an ultrasound machine, a nuclear imaging machine, and/or a PET CT machine.

Optionally, the 3D images are represented and/or stored and/or may be presented as 2D sequential 2D slices, for example, 2D axial slices of a 3D CT scan volume. When 2D slices are not available (e.g., from the PACS), the 2D slices may be computed and/or created from the 3D image.

The 3D images may be referred to herein as 3D volumes.

At 104, point clouds are extracted from, and/or computed from, the 3D anatomical images. A single point cloud may be extracted from each 3D anatomical image. Each point cloud depicts the target anatomical structure of the respective 3D anatomical image.

Each point cloud is represented by an ordered list of coordinates. Optionally, each point cloud denotes a 3D polygon mesh represented by coordinate order of the vertices and connections thereof. A certain shape may be described by many permutations of the same list. The order of the list does not necessarily have meaning to the shape it describes, however, in order to have a single representation for the entire dataset, a single order (which may be arbitrary) is set to represent the different points clouds (e.g., all point clouds). This may be done, for example, by projecting a selected template structure of the same type (e.g., a certain femur) and mapping the template in a non-rigid fashion onto all other femurs, as described herein in additional detail. Using this process, the template defines the shape of the femurs of the dataset (e.g., any femur from all the femurs) and maintains constant ordering.

Optionally, each point cloud is extracted from the respective 3D anatomical image by processing the 2D slices of the 3D image, according to the following exemplary process: A 2D segmentation of the depicted target anatomical structure is computed for each 2D slice of the respective 3D image. The 2D segmentation of the depicted target anatomical structured may be segmented from the respective 2D slice by a segmentation convolutional neural network that is fed a 2D image and outputs a pixel-wise probability of respective pixels depicting the target anatomical structure. The segmentation neural network may be trained on a training dataset of 2D slices of 3D anatomical images of sample patients, optionally sequential 2D slices, for example, axial slices and/or other views. Each 2D slice is annotated with an indication of a segmentation of the target anatomical structure, for example, using a polygon and/or other segmentation indication. The annotation of the 2D slices of the training dataset denotes ground truth for the training process. The segmentation may be manually annotated by a user and/or automatically by code trained to segment 2D images. The 2D segmentations computed for the 2D slices (optionally all the 2D slices) of the respective 3D image by the segmentation neural network are stacked. A 3D binary array of the target anatomical structure (optionally the whole structure) is obtained (e.g., computed) from the stacked 2D segmentations. Optionally, the created 3D binary array is post-processed, for example, to ensure smooth, accurate, and/o properly scaled 3D array of the target anatomical structure.

The point cloud is computed from the 3D binary array. Optionally, a mesh is computed from the 3D binary array. The mesh may be used to create the 3D point cloud, for example, using the marching cubes process.

Figure 4:
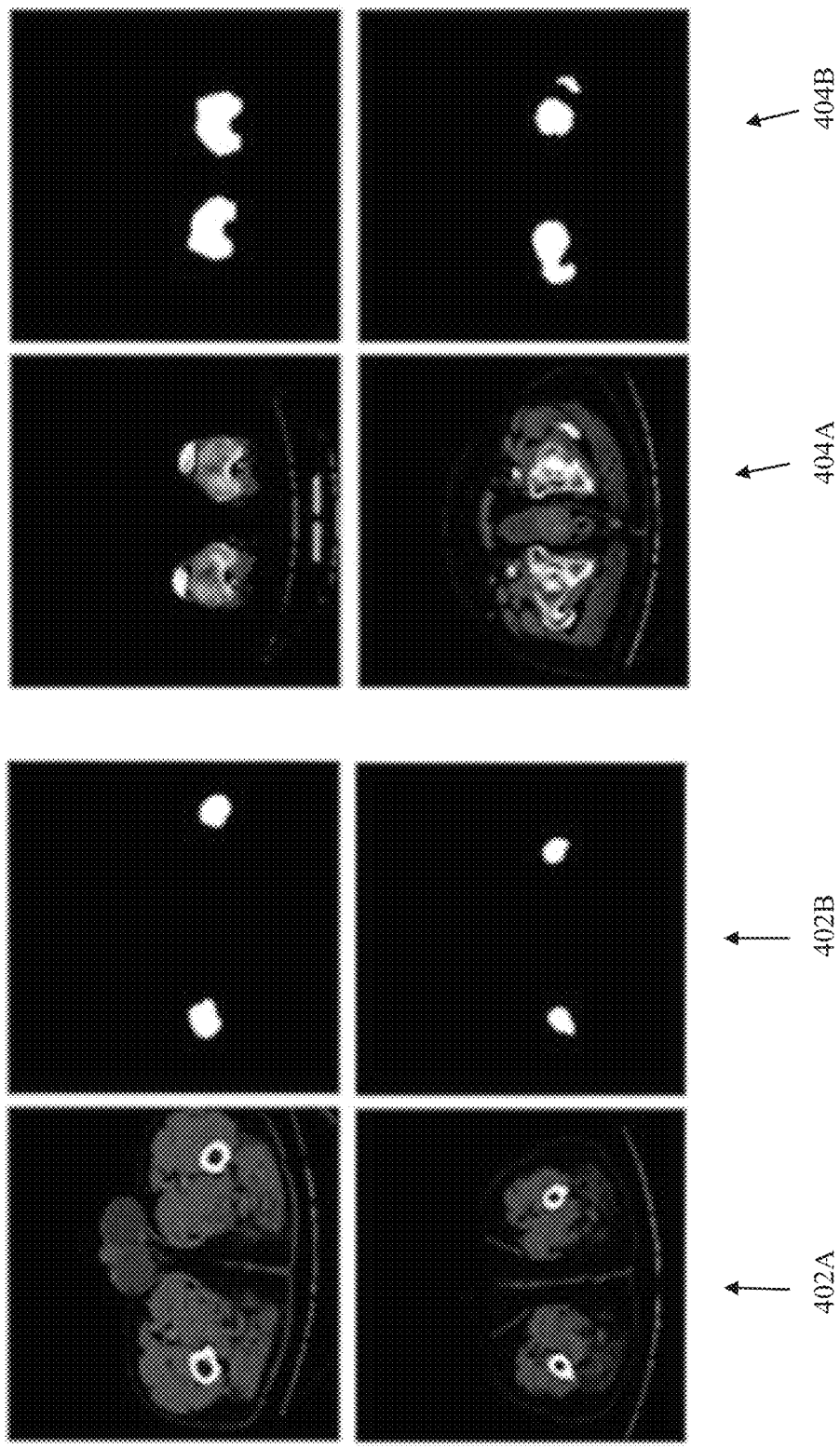
FIG. 4 is a schematic of an automated segmentation of a femur (i.e., the target anatomical structure) from a 3D CT scan volume, in accordance with some embodiments of the present invention.

Reference is now made to FIG. 4, which is a schematic of an automated segmentation of a femur (i.e., the target anatomical structure) from a 3D CT scan volume, in accordance with some embodiments of the present invention. The femur is segmented slice by slice (i.e., from sequential 2D images of the 3D volume) by stacking the segmented portions into a 3D array, as described herein. Images 402A and 404A depict examples of raw CT slices. Images 402B and 404B depict the results of the segmentation of the corresponding respective slice 402A and 404A.

Figure 5:
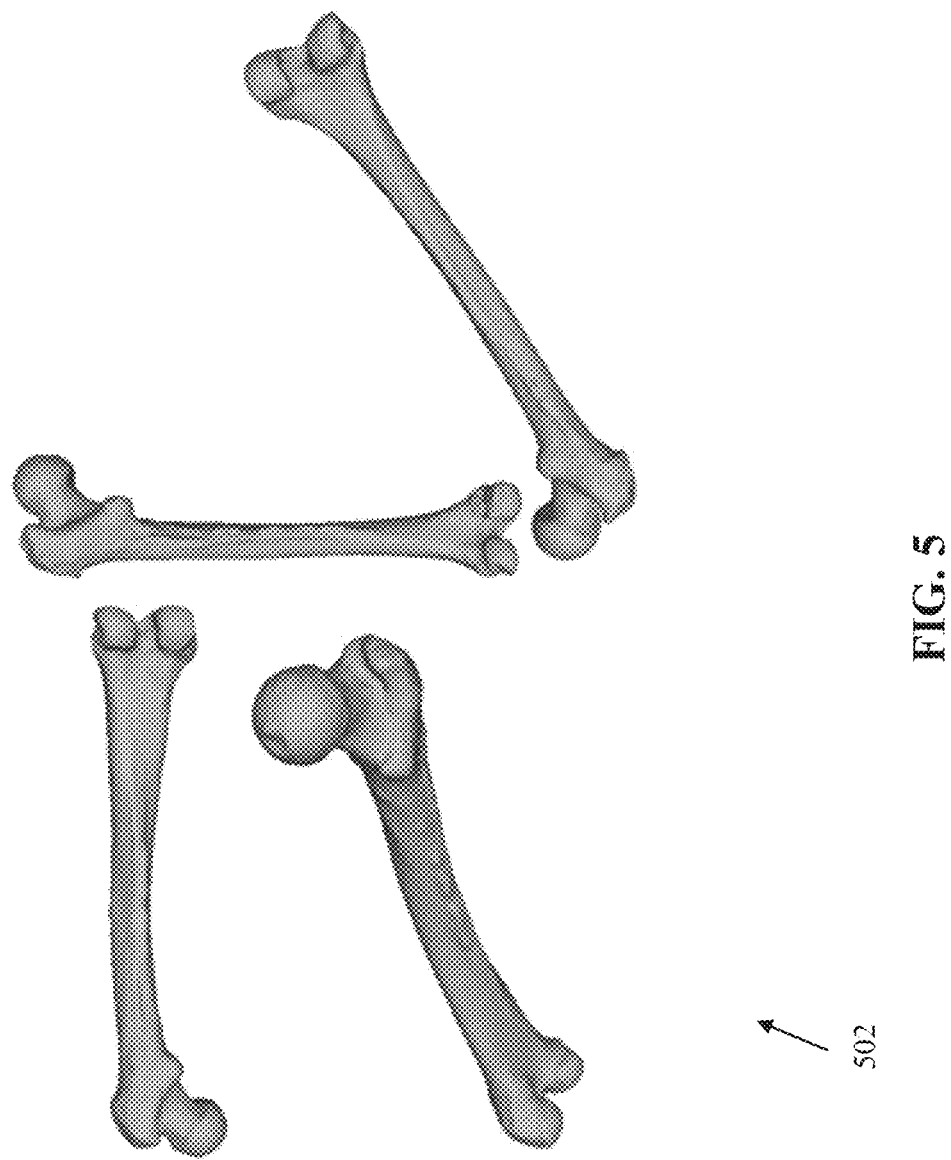
FIG. 5 is a schematic of different views of a segmented 3D femur and mesh generated from the CT scan volume, in accordance with some embodiments of the present invention.

Reference is now made to FIG. 5, which is a schematic of different views of a segmented 3D femur 502 and mesh generated from the CT scan volume, in accordance with some embodiments of the present invention. A comparison performed by Inventors between the automated 3D segmentation process described herein and manual segmentation of the femur bone shows an RMSE of 0.5 millimeters. 3D femur is created from the 2D segmentation of the slices of the CT volume, as depicted with reference to FIG. 4.

Referring now back to FIG. 1, at 106, selecting one of point clouds is selected as a template.

At 108, a warped template is computed for each of the other point clouds (i.e., which were not selected to be used as the template) of the 3D images according to the template. The template may be selected, for example, randomly, taking the first template, taking the last template, taking a template from a certain location. It is noted that any template may be suitable.

Each respective warped template may be computed by registering, optionally non-rigidly registering, the template with each of the point clouds. The respective warped template has a shape of the respective point cloud and retains the coordinate order of the template. The computed warped templates are consistent in terms of coordinate order.

Exemplary non-rigid registration processes include, for example, coherent point drift and/or non-rigid iterative closest points.

At 110, 2D images depicting the target anatomical structure are received. The 2D images may be from the same sample patients and of the same target anatomical structures depicted in the 3D anatomical images.

Optionally, one or more 2D images are received for each target anatomical structure of each sample individual. The 2D images may depict different orientations relative to the target anatomical structure, for example, AP, lateral, different sensor tilt angles, and/or other orientations. The 2D images may be based on radiological standards for acquiring x-rays (or other images such as ultrasound), for example, three views of the abdomen, multiple views of a joint, and the like.

Optionally, the 2D images are 2D emulated images (also referred to as pseudo images) created from the received 3D anatomical images, for example, pseudo x-rays (also referred to as radiographs). The 2D images may be computed by aggregating imaging values (e.g., pixel and/or voxel intensity values) of the corresponding 3D anatomical image. Exemplary aggregation methods include: integrating, summing, weighted average. For example, aggregating the pixel and/or voxel intensity values along a direction corresponding to an orientation of a virtual 2D sensor virtually capturing the emulated 2D anatomical image. Conceptually, the 3D volume is "compressed" into a 2D area along an axis to obtain the 2D image at a desired plane.

Optionally, the emulated 2D anatomical images are computed to correspond to target 2D x-ray images captured by an x-ray source and x-ray sensor array at a predefined orientation relation to the patient. For example, the emulated images computed from the 3D volume (e.g., CT scan) are statistically similar to 2D x-ray images captured by an x-ray machine.

For example, a pseudo x-ray is generated from a CT volume generated by a CT scanner, by integrating the digital levels of the CT volume along directions defined by rays casted from a virtual x-ray source to the pixels of the virtual x-ray sensor array.

The process of generating emulated 2D images (e.g., pseudo radiographs) from 3D images creates emulated 3D image that appear similar to actual radiographs. For example, statistically similar within a requirement, and/or where a user has difficulty or is unable to tell which 2D image is a real and original 2D image and which is an emulated 2D image. Moreover, the emulated 3D image may be generated in different source-patient-sensor configurations, and/or sensor resolutions, and/or sensor pitch.

Alternatively or additionally, 2D anatomical images depicting the target anatomical structure depicted in corresponding 3D anatomical images are captured by a 2D imaging device. For example, during the 3D CT scan, a 2D x-ray image is also captured by an x-ray imaging device.

Optionally, the 2D emulated images are computed to create 2D images at imaging planes that may be captured by real world 2D imaging devices (e.g., x-ray machines, ultrasound), for example, AP, lateral, and other standard orientations such ax axial and/or other planes obtained by ultrasound machines.

At 112, training dataset is created from the warped templates and the corresponding 2D images, optionally the emulated 2D images.

Multiple training datasets may be created, for example, each training dataset to train a respective neural network. Training dataset may be created, for example, according to target anatomical structure (e.g., for femur bone, for spinal vertebra, for knee joint), and/or according to imaging modality outputting the 2D images, for example, x-ray and ultrasound.

The training dataset may include 3D point cloud models of various sizes and/or shapes, represented in a consistent manner.

At 114, a neural network is trained according to the training dataset. The warped templates represent a ground truth. The 2D images, optionally emulated 2D images, represent input. The neural network is trained to mapping one or more 2D anatomical image fed into the neural network into a 3D point cloud output of the network.

The 3D point clouds of the training dataset act as the target and/or ground truth when training the neural network. Variation between a ground truth 3D point cloud model and the neural network's prediction results in a loss term that the training process minimizes.

Multiple neural networks may be trained according to respective training datasets.

In some implementations, the neural network may be represented as an encoder-decoder. The input 2D image(s) are decomposed into a set of features which hold the information required for the 3D object shape prediction, which may represent the encoding part of the neural network. The second part of the neural network may be represented as a decoder. The second part receives the feature vector extracted from the 2D images by the encoder, and converts the feature vector into a full 3D model. During training, the network is fed with the 2D images (e.g., pseudo images, optionally radiograph(s)) and outputs (e.g., predicts) the object's 3D structure. From the predicted structure and the ground truth structure, an error (also referred to as loss) term is calculated. During training, the network gradually varies its internal parameters so that the loss term is reduced and the predicted object's 3D structure gradually becomes more and more similar to the ground truth structure. Once the neural network is trained, it is used to output (e.g., predict) the 3D shape of objects based on new 2D images (e.g., radiographs) it has not been trained on. The neural network is fed with 2D images (e.g., radiograph(s)) and outputs the coordinates of the 3D anatomical structured depicted in the 2D radiograph(s).

Reference is now made to FIG. 6, which is a diagram depicting an exemplary architecture of the neural network for mapping two 2D anatomical images into a 3D point cloud, in accordance with some embodiments of the present invention. The two 2D images may be x-ray images. The two 2D images may be of different views of the target anatomical image, for example, an anterior-posterior (AP) and lateral views.

Referring now back to FIG. 1, at 116, the trained neural network is provided. For example, the trained neural network may be stored on a server that handles requests to output 3D point clouds in response to 2D image(s), may be forwarded to remote client terminals for local computing of 3D point clouds, and/or may be stored on a storage device.

Referring now back to FIG. 3, at 302, one or more trained neural network are provided and/or trained (e.g., as described with reference to FIG. 1), for example, according to target anatomical structure and/or according to imaging modality machine outputting the 2D image(s) that are fed into the neural network (e.g., x-ray, ultrasound).

The neural network is trained according to a training dataset of warped templates and corresponding 2D images, as described herein. The warped templates may be created from point clouds extracted from 3D anatomical images.

Each point cloud is represented by an ordered list of coordinates. One of the point clouds is selected as a template. The template may be non-rigidly registered with each of the other (i.e., non-selected) point clouds to compute a respective warped template. Each warped template has a shape of the respective point cloud and retains the coordinate order of the template. The warped templates are consistent in terms of coordinate order.

At 304, one or more 2D anatomical images depicting a target anatomical structure of a target patient are obtained. The 2D anatomical images may be acquired based on radiological and/or clinical standards. For example, the 2D anatomical image(s) are x-ray image(s) outputted by an x-ray machine, for example, AP and/or lateral views (e.g., of the chest, femur), three views of the abdomen, and two or more views of a joint. In another example, the 2D anatomical images are ultrasound images, for example, axial planes, or other views of different organs such as different planes of the liver.

At 306, the 2D anatomical image(s) are fed into the neural network.

At 308, a reconstructed 3D point cloud model of the target anatomical structure is outputted by the trained neural network, as described herein.

Optionally, the reconstructed 3D point cloud model of the target anatomical structure depicts an internal surface of the target anatomical structure, for example, an inner surface of an inner cavity and/or lumen. For example, when the target anatomical structure is a long bone, the internal surface depicted in the reconstructed 3D point cloud may be an inner surface of a medullary cavity of the long bone. In another example, when the target anatomical structure is a bladder the internal surface is the internal surface of the bladder.

At 310, a conversion parameter may be computed for converting the pixel and/or voxel units of the reconstructed 3D image to millimeters (or other real world measure).

The following is an exemplary process for computing the conversion parameter: a projection is computed for projecting the reconstructed 3D model on the plane of the 2D image (which was fed into the neural network that outputted the reconstructed 3D image). The 2D anatomical image includes a depiction of a calibration object having known dimensions, for example, a steel ball having a known diameter. The calibration object may be selected to appear clearly on the 2D images, for example, made of radio-opaque material to appear in x-rays. A scale parameter of the projection is computed. The reconstructed 3D model is scaled from original arbitrary units to pixel and/or voxel units according to the scale parameter. A conversion parameter is computed for converting from pixel and/or voxel units to millimeters (or other real world physical measurement, such as centimeters) according to the calibration object depicted in the 2D anatomical image. The pixel and/or voxel units of the reconstructed 3D image may be converted to millimeters according to the computed conversion parameter.

Reference is now made to FIG. 7, which is 2D x-ray images 702 and 704 depicting use of a calibration object 706 (implemented as a steel ball) placed to a femur 708 (i.e., .target anatomical structure), where calibration object 706 is automatically detected and measured for converting the size of a reconstructed 3D point cloud 710 of femur 708 from arbitrary units to real world size, in accordance with some embodiments of the present invention. 3D reconstructed point cloud 710 is shown projected on 2D femur 708 in 2D x-ray image 704. Calibration object 706 is automatically detected, as denoted by outline 712 in 2D x-ray image 702.

Referring now back to FIG. 3, at 312, surgical treatment of the target anatomical structure of the patient may be planned according to the reconstructed 3D point cloud model of the target anatomical structure.

Exemplary surgical treatment of the patient planned according to the reconstructed 3D point cloud model of the target anatomical structure includes: selecting a joint replacement prosthetics, and/or a fracture repair implantable device (e.g., screw, nail, intermedullary nail). Another example of planning surgical treatment is based on an analysis of the 3D point cloud to determine where to place the prosthetic and/or fracture repair device, for example, how to insert nails in order to reduce the fracture.

The components for surgical treatment of the patient may be sized and/or selected according to dimension(s) of the bone (and/or other structure) depicted by the 3D point cloud model, optionally based on the computed conversion into millimeters. For example, sizes of intermedullary nails, sizes of screws, and/or to sizes of prosthetic joints, for treatment of the patient.

Optionally, surgical treatment of the patient is planned according to the reconstructed 3D point cloud model of the target anatomical structure by simulating a surgical procedure using the 3D point cloud model, for example, using a surgical simulation application.

In another example, a user may view the 3D point cloud in a viewing application. The user may manually manipulate the 3D point cloud, for example, perform measurements, and/or change viewing orientation.

At 314, the patient may be treated according to the planning based on the 3D point cloud model, for example, using the selected prosthesis and/or fracture reduction devices, and/or inserted according to the planned surgery.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant 3D anatomical images will be developed and the scope of the term 3D anatomical image is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of training a neural network for reconstructing of a 3D point cloud from at least one 2D image, comprising:

extracting a plurality of point clouds each represented by an ordered list of coordinates, from a plurality of 3D anatomical images depicting a target anatomical structure;

selecting one of the plurality of point clouds as a template;

non-rigidly registering the template with each of the plurality of point clouds to compute a respective warped template having a shape of the respective point cloud and retaining the coordinate order of the template, wherein the plurality of warped templates are consistent in terms of coordinate order;

receiving a plurality of 2D anatomical images depicting the target anatomical structure depicted in corresponding 3D anatomical images; and training a neural network, according to a training dataset of the warped templates and corresponding 2D images, for mapping at least one 2D anatomical image into a 3D point cloud.

2. The method of claim 1, wherein the plurality of 2D anatomical images comprise a plurality of emulated 2D anatomical images computed from each of the corresponding 3D anatomical images, by aggregating imaging values of the corresponding 3D anatomical image along a direction corresponding to an orientation of a virtual 2D sensor virtually capturing the emulated 2D anatomical image.

3. The method of claim 2, wherein the plurality of emulated 2D anatomical images are computed to correspond to target 2D x-ray images captured by an x-ray source and x-ray sensor array at a predefined orientation relation to the patient.

4. The method of claim 1, wherein each of the plurality of point clouds extracted from the plurality of 3D anatomical images denotes a 3D polygon mesh represented by coordinate order of the vertices and connections thereof.

5. The method of claim 1, wherein each point cloud of the plurality of point clouds is extracted from a respective 3D anatomical image of the plurality of 3D anatomical images by:

computing, for each 2D slice of a plurality of 2D slices of the respective 3D anatomical image, a 2D segmentation of the depicted target anatomical structure, stacking the plurality of 2D segmentations computed for the plurality of 2D slices, obtaining a 3D binary array of the target anatomical structure from the stacked plurality of 2D segmentations, and computing the point cloud from the 3D binary array.

6. The method of claim 5, wherein the 2D segmentation of the depicted target anatomical structured is segmented from the respective 2D slice by a segmentation neural network that computes a pixel-wise probability of the respective pixel depicting the target anatomical structure, wherein the segmentation neural network is trained on a training dataset of a plurality of 2D slices of each a plurality of 3D anatomical images of a plurality of sample patients, wherein each 2D slice is annotated with an indication of a segmentation of the target anatomical structure.

7. The method of claim 1, wherein the non-rigidly registering is performed according to a non-rigid registration process selected from coherent point drift and non-rigid iterative closest points.

8. The method of claim 1, wherein the target anatomical structure includes a joint and associated bones, selected from the group consisting of: a hip joint, a knee joint, and a shoulder joint.

9. The method of claim 1, wherein the target anatomical structure comprises a bone.

10. The method of claim 9, wherein the target anatomical structure comprises a femur.

11. The method of claim 1, wherein the target anatomical structure includes an inner surface of a bone.

12. The method of claim 11, wherein the inner surface comprises an inner surface of a cortical bone.

13. The method of claim 11, wherein the inner surface is of a medullary cavity of a long bone.

14. A method for surgical treatment of a target anatomical structure of a patient, comprising:
  obtaining a 2D anatomical image depicting a target anatomical structure of a target patient;
  inputting the 2D anatomical image into a trained neural network trained according to a training dataset of a plurality of warped templates and corresponding 2D images,
  wherein the plurality of warped templates are created from a plurality of point clouds extracted from a plurality of 3D anatomical images, each point cloud represented by an ordered list of coordinates, one of the plurality of point clouds is selected as a template, the template is non-rigidly registered with each of the plurality of point clouds to compute the plurality of warped template each having a shape of the respective point cloud and retaining the coordinate order of the template, wherein the plurality of warped templates are consistent in terms of coordinate order; and
  outputting a reconstructed 3D point cloud model of the target anatomical structure by the trained neural network,
  wherein surgical treatment of the target anatomical structure of the patient is planned according to the reconstructed 3D point cloud model of the target anatomical structure.

15. The method of claim 14, wherein the reconstructed 3D point cloud model of the target anatomical structure includes an internal surface thereof.

16. The method of claim 15, wherein the target anatomical structure comprises a long bone and the internal surface depicted in the reconstructed 3D point cloud comprises an inner surface of a medullary cavity of the long bone.

17. The method of claim 14, wherein the 2D anatomical images comprises an x-ray image.

18. The method of claim 14, further comprising:
  computing a projection for projecting the reconstructed 3D model on the plane of the 2D image, wherein the 2D anatomical image includes a depiction of a calibration object having known dimensions;
  computing a scale parameter of the projection;
  scaling the reconstructed 3D model from original arbitrary units to pixel units according to the scale parameter;
  computing a conversion parameter for converting from pixel units to millimeters according to the calibration object depicted in the 2D anatomical image; and
  converting the pixel units of the reconstructed 3D image to millimeters according to the computed conversion parameter.

19. The method of claim 14, wherein the target anatomical region comprises at least one bone, and surgical treatment of the patient planned according to the reconstructed 3D point cloud model of the target anatomical structure comprises selecting at least one of a joint replacement prosthetic and a fracture repair implantable device according to at least one dimension of the at least one bone depicted by the 3D point cloud model.

20. The method of claim 14, wherein surgical treatment of the patient planned according to the reconstructed 3D point cloud model of the target anatomical structure comprises simulating a surgical procedure using the 3D point cloud model.

21. A system for training a neural network for reconstructing of a 3D point cloud from a 2D image, comprising:
  at least one hardware processor executing a code for:
    extracting a plurality of point clouds each represented by an ordered list of coordinates, from a plurality of 3D anatomical images depicting a target anatomical structure;
    selecting one of the plurality of point clouds as a template;
      non-rigidly registering the template with each of the plurality of point clouds to compute a respective warped template having a shape of the respective point cloud and retaining the coordinate order of the template, wherein the plurality of warped templates are consistent in terms of coordinate order;
    receiving a plurality of 2D anatomical images depicting the target anatomical structure depicted in corresponding 3D anatomical images; and
    training a neural network, according to a training dataset of the warped templates and corresponding 2D images, for mapping at least one 2D anatomical image into a 3D point cloud.

* * * * *